(12) United States Patent
Fisher

(10) Patent No.: US 9,044,418 B2
(45) Date of Patent: Jun. 2, 2015

(54) TREATMENT FOR DEPRESSION AND OTHER MENTAL CONDITIONS WITH SYNTHETIC ISOTOPE-MODIFIED LITHIUM

(71) Applicant: Matthew P. A. Fisher, Santa Barbara, CA (US)

(72) Inventor: Matthew P. A. Fisher, Santa Barbara, CA (US)

(*) Notice: Subject to any disclaimer, the term of this patent is extended or adjusted under 35 U.S.C. 154(b) by 0 days.

(21) Appl. No.: 14/512,292

(22) Filed: Oct. 10, 2014

(65) Prior Publication Data

US 2015/0104528 A1 Apr. 16, 2015

Related U.S. Application Data

(60) Provisional application No. 61/890,103, filed on Oct. 11, 2013.

(51) Int. Cl.
*A61K 33/00* (2006.01)
*A61K 33/14* (2006.01)
*A61K 8/19* (2006.01)

(52) U.S. Cl.
CPC . *A61K 33/00* (2013.01); *A61K 8/19* (2013.01); *A61K 33/14* (2013.01)

(58) Field of Classification Search
CPC .................. A61K 8/19; A61K 33/14
See application file for complete search history.

(56) References Cited

U.S. PATENT DOCUMENTS 5,415,878 A * 5/1995 Newton et al. ................ 424/722

OTHER PUBLICATIONS

Alexander et al, Differential Lethality of Lithium Isotopes in Mice, Biological Psychiatry, vol. 15, No. 3, 1980, pp. 469-471.*
Lieberman et al, Characteristics of the Uptake of lithium Isotopes in Erythrocytes, Biological Psychiatry, vol. 14, No. 5, 1979, pp. 845-849.*
K. Lieberman, G. J. Alexander and J.A. Sechzer, "Stable Isotopes of Lithium: Dissimilar Biochemical and Behavioral Effects," Experientia 42, 1986, pp. 985-987.

"Li Effect on Rat Behavior and Offspring," Biol Psychiatry, vol. 21, p. 1261,Table 2. 1986.
Perry F. Renshaw, "A Diffusional Contribution to Lithium Isotope Effects," Biol Psychiatry, 1987, vol. 22, pp. 73-78.
K.W. Lieberman, G. J. Alexander, P. Stokes, "Dissimilar Effects of Lithium Isotopes on Motility in Rats," Pharmacology Biochemistry & Behavior, Feb. 3, 1979, vol. 10, pp. 933-935, USA.
G.J. Alexander, K.W. Lieberman, M. Okamoto, P.E. Stokes, and E. Triana, Lithium Toxicology: Effect of Isotopic Composition on Lethality Behavior, 1982, Pharmacology Biochemistry & Behavior, vol. 16, pp. 801-804, USA.
William R. Sherman, Ling Y. Munsell, and Yun-Hua H. Wong, "Differential Uptake of Lithium Isotopes by Rat Cerebral Coretx and its Effect on Inositol Phosphate Metabolism," Journal of Neurochemistry, 1984, vol. 42, No. 2, pp. 880-882, International Society for Neurochemistry, Raven Press, New York.
Jeri A. Sechzer, Kenneth W. Lieberman, George J. Alexander, David Weidman, and Peter E. Stokes, "Aberrant Parenting and Delayed Offspring Development in Rats Exposed to Lithium," Biol Psychiatry, 1986, vol. 21, pp. 1258-1266.
Stokes M P., Lieberman, K.W. Okamoto, M. and Alexander, G., Biol. Psychiatry, Stable Isotopes of Li: in Vivo Differential Distribution Between Plasma and Cerebrospinal Fluid, 17, 1982, pp. 413-421.
R. Parthasarthy and Eisenberg Jr., Annals New York Academy of Sciences, Lack of Differential Lethality of Lithium Isotopes in Mice, 435, 463-465, 1984.
Peter M. Stoll, Peter E. Stokes and Michiko Okamoto, "Lithium Isotopes: Differential Effects on Function and Histology," Bipolar Disorders, 2001, Ireland, 174-180.
Catherine Heurteaux, Camille Ripoll, Said Ouznadji, Houria Ouznadji, Jean-Claude Wissocq and Michel Thellier, "Lithium Transport in the Mouse Brain," Brain Research, 547, 1991, pp. 122-128.

* cited by examiner

*Primary Examiner* — Benjamin Packard
(74) *Attorney, Agent, or Firm* — Cislo & Thomas, LLP

(57) ABSTRACT

Treating mental illness by administering synthetic isotope-modified lithium compounds: (i) with the lithium-6 isotope making up at least 95% of the total number of lithium atoms in the compound to treat depression and other mental conditions with reduced alertness levels, (ii) with the lithium-7 isotope making up at least 95% of the total number of lithium atoms in the compound to treat mania and bipolar disorder and other mental illnesses which respond to lithium compounds with natural isotope abundance levels, (iii) with the lithium-6 isotope ranging from 10% to 95% of the total number of lithium atoms in the compound individually tailored to treat patients with a broad variety of mental disorders, including those in (i) and (ii) above.

19 Claims, No Drawings

TREATMENT FOR DEPRESSION AND OTHER MENTAL CONDITIONS WITH SYNTHETIC ISOTOPE-MODIFIED LITHIUM

CROSS-REFERENCE TO RELATED APPLICATION

This patent application claims the benefit of U.S. Provisional Patent Application Ser. No. 61/890,103, filed Oct. 11, 2013, entitled "Isotope-Modified Lithium Carbonate," which applications incorporated in its entirety here by this reference.

TECHNICAL FIELD

This invention relates to a new class of psychiatric medications to treat depression and other mental conditions.

BACKGROUND

Lithium as a Pharmaceutical

In 1949, John Cade demonstrated the efficacy of lithium in modifying the mood of patients suffering from certain psychiatric disorders. Administrating lithium-carbonate ($Li_2CO_3$) to patients with mania had a dramatic effect in tempering their mania and stabilizing their mood, although depressed patients were less responsive. Cade's discovery, reported in the paper "Lithium Salts in the Treatment of Psychotic Excitement," prompted further research, and in 1970 lithium-carbonate was approved by the U.S. FDA for the treatment of mania and bipolar disorder. Lithium citrate ($Li_3C_6H_5O_7$) is also FDA approved for mania (and bipolar disorder). The discovery of lithium's role as a mood suppressant and stabilizer was later hailed by the award winning author Kay Redfield Jamison as "one of the most important advances in modern psychiatry."

Like any psychiatric pharmaceutical, however, lithium is only effective in treating a restricted class of mental disorders. While lithium is, to this day, perhaps the best treatment for mania and other mental disorders with a strong manic component, like bipolar disorder, it is largely ineffective and seldom used in treating psychotic disorders such as schizophrenia and schizo-effective disorders or in treating (unipolar) major depression. Moreover, there are patients suffering from mania who are not treated effectively with lithium. Anti-psychotic medications, especially clozapine, can reduce the suffering of some schizophrenic patients, and there are several classes of anti-depressants (for example the tri-cyclic antidepressants, Wellbutrin and serotonin-re-uptake inhibitors, the SSRI's, such as Prozac) which have been effective in treating patients with depression and other mental disorders with reduced or impaired cognitive functioning. However, there are patients with mental illness whose conditions are drug-resistant. Electro-shock therapy has been effective at treating some drug-resistant patients with major depression, and magnetic stimulation techniques such as transcranial magneto-stimulation (TMS) does appear to benefit some depressed patients.

All psychiatric pharmaceuticals can, and usually do, have unwanted side effects, which range across a broad spectrum (such as suppression of sexual libido especially problematic for the SSRI's, increased heart-beat rates and reduced blood pressure quite serious for the tri-cyclic anti-depressants). Patients on some psychiatric medications require regular blood monitoring to prevent toxicity, such as monitoring white blood cell counts for patients taking clozapine to reduce the risk of agranulocytosis which can be fatal, and monitoring lithium blood levels to diminish the risk of kidney damage for those patients taking lithium. Electro-shock therapy can cause short-term and occasionally long term memory loss. The short-term side effects of transcranial magneto-stimulation are mild although the rare occurrence of induced seizures is an acute risk. In view of the incredible human toll that mental disorders inflict, not to mention the economic impact, there is a pressing need for new psychiatric pharmaceuticals and treatments.

SUMMARY OF THE INVENTION

This invention concerns a new method to treat depression and other mental conditions in patients who do not respond adequately to present treatments, using a new class of synthetically modified lithium pharmaceuticals obtained by altering the natural isotope abundance of lithium-6 and lithium-7 in lithium-carbonate and other lithium compounds. Modifying the natural isotope abundance of the atoms in any medical chemical compound to change its efficacy is unprecedented. The natural abundance of lithium-7 is very high. The lithium-7 isotope makes up 92.5% of all lithium atoms with the rarer lithium-6 isotope making up only 7.5% of the lithium atoms. These lithium-7 and lithium-6 concentrations are present in all naturally occurring lithium compounds and in all lithium pharmaceuticals. This invention concerns a new treatment for depression and other mental conditions with synthetically purified lithium-6 compounds (meaning with the lithium-6 isotope making up over 95% of the total lithium atoms in the compound), lithium-6 enriched compounds (meaning with lithium-6 isotope making up between 10% and 95% of the total lithium atoms in the compound), lithium-7 purified compounds (meaning with lithium-7 isotope in amounts greater than 99% of the total lithium atoms in the compound), and lithium-7 enriched compounds (meaning with lithium-7 isotope in amounts between 95% and 99% of the total lithium atoms in the compound). "Dialing" the lithium isotope concentration away from the natural abundance level may provide a large class of new synthetic psychiatric pharmaceuticals that could be individually tailored to achieve maximum efficacy in treating patients suffering from a broad spectrum of mental disorders.

DETAILED DESCRIPTION OF THE INVENTION

The detailed description set forth below is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present invention is directed towards a new treatment for depression and other mental conditions using a new class of synthetically modified lithium pharmaceuticals obtained by altering the natural isotope abundance of lithium-6 and lithium-7. The synthetically modified lithium pharmaceuticals of the present invention may be used to alleviate one or more symptoms of the mental condition.

Lithium Isotopes and Biochemistry

The primary source of the lithium element is naturally occurring lithium carbonate ($Li_2CO_3$). The lithium carbonate molecule consists of a central carbon atom bonded to the oxygen ions, with two oxygen ions each bonded to a lithium ion. The electron valence of the constituent atoms dictates both the molecular structure and the chemical and biochemical reactions of the molecule.

Many atoms come in several stable isotopes, distinguished by the number of neutrons inside their atomic nucleus. Lithium has two stable isotopes, lithium-7 with 4 neutrons and lithium-6 with 3 neutrons. In nature, 92.5% of lithium atoms are lithium-7 while lithium-6 constitutes the other 7.5%.

By and large, biology is insensitive to the different atomic isotopes; exceptions being heavy water (hydrogen replaced by deuterium) which does have certain biological signatures, such as lengthening the period of some circadian oscillations, reducing the rate of plant growth, and causing dizziness when ingested by humans. Additionally, an experiment from 1986 reported that, while female mother rats fed lithium had "low" state of alertness compared to control rats fed a placebo, female rats fed lithium-6 had elevated alertness levels, reported as a "very high" state of alertness compared to the control rats. Therefore, it is the applicant's belief that synthetic lithium-6 purified compounds, comprised predominantly of lithium-6 (greater than 95% of the total lithium), may be effective at treating mental conditions with reduced alertness levels, such as chronic and major depression—disorders that are not well treated with the present lithium pharmaceuticals which all have the natural lithium-isotope abundance concentrations (i.e. 92.5% lithium-7 and only 7.3% lithium-6). Purifying lithium-6 requires synthetic means, since all naturally occurring lithium (as mined from dried lake beds, for example) contain the natural abundance of the lithium isotopes.

Synthetic Lithium Pharmaceuticals

Isotope-Modified Lithium Compounds in naturally occurring lithium compounds, such as lithium carbonate, the concentration of lithium-7 and lithium-6 atoms matches nature's ratio—92.5% lithium-7 and 7.5% lithium-6. But, this concentration ratio can be modified by synthetic means, and synthetic isotope-modified lithium compounds may be used to treat various psychiatric disorders and conditions, including those resistant to existing medications. Four classes of isotope-modified lithium compounds are considered. The amounts of lithium, dosages, concentrations, and the like are provided as approximations to account for variations in manufacturing tolerances.

Li-6-Purified Compounds:

As used in this application, a purified Li-6 compound is any lithium containing compound with lithium-6 present in an amount of at least 95% of the total lithium (i.e. lithium-6 and lithium-7) in the compound. The 95% threshold is much higher than the 7.5% natural abundance of lithium-6 that occurs in present (un-synthesized) lithium pharmaceuticals, and is close to the ideal limit of lithium compounds with 100% lithium-6. Synthetic means are required to attain these high lithium-6 concentrations.

Li-7-Purified Compounds:

As used in this application, a Li-7-purified compound is any lithium containing compound with the percentage of lithium-7 present in the compound being at least 99% of the total lithium content. This lithium-7 concentration is significantly higher than the 92.5% natural abundance of lithium-7. The Li-7-purified compounds have very low lithium-6 concentrations (below 1%), much lower than the 7.5% natural lithium-6 abundance. Synthetic means are required to attain such high lithium-7 and low lithium-6 concentrations.

Li-6-Enriched Compounds:

As used in this application, a Li-6-enriched compound is any lithium containing compound with the percentage of lithium-6 present in the compound greater than 10% but less than 95% of the total lithium content. The 10% lithium-6 is appreciably larger than the natural lithium-6 abundance of 7.5%. While lithium-6 concentrations in Li-6-enriched compounds can, in principle, be varied arbitrarily—in practical terms, it may be possible to control the concentration in increments of 10%. By way of example only, the following are eight different compounds in the Li-6-enriched compound class, with lithium-6 concentrations in the approximate ranges, 10%-25%, 25%-35%, 35%-45%, 45%-55%, 55%-65%, 65%-75%, 75%-85% and 85%-95%. The average lithium-6 concentrations in these eight compounds will be, approximately 20%, 30%, 40%, 50%, 60%, 70%, 80% and 90%, respectively. Synthetic means will be required to dial these lithium-6 concentrations.

Li-7-Enriched Compounds:

As used in this application, a Li-7-enriched compound is any lithium containing compound with the percentage of lithium-7 present in the compound greater than 95% but less than 99% of the total lithium content. The 95% lithium-7 is larger than the natural lithium-7 abundance of 92.5%, while below the 99% lithium-7 in the Li-7-purified compound.

Psychiatric Functionalities

The above isotope-modified lithium compounds may be used effectively as active ingredients in pharmaceutical compositions for treating mental conditions. The efficacy of treatment for a given mental condition will depend on the lithium-6 and lithium-7 isotope concentrations in the corresponding lithium-containing pharmaceutical.

Functionality of Li-6-Purified Compounds

Lithium-containing compounds with very high concentrations of lithium-6 (above 95% of the total lithium atoms) may be most effective in treating major depression and other mental conditions involving diminished alertness levels and/or memory recall, and overall lowered mental functionality levels. In addition to major depression, these conditions could include chronic depression, attention deficit disorder, amnesia and possibly dementia. These mental disorders are not effectively treated by present lithium pharmaceutical compounds, which all have much lower concentration of lithium-6 (the natural abundance of 7.5%).

Functionality of Li-7-Enriched and Li-7-Purified Compounds

Present lithium pharmaceuticals (i.e. compounds approved by the FDA) are comprised of lithium-7 and lithium-6 isotopes with their natural abundance levels (92.5% lithium-7 and 7.5% lithium-6). These lithium pharmaceuticals are effective at tempering mania and manic swings in bipolar disorders. The synthetic Li-7-enriched and Li-7-purified compounds with larger lithium-7 concentrations (above 95% lithium-7) might be even more effective at treating these mental disorders, perhaps requiring somewhat lower dosages. Li-7-purified compounds might be especially helpful in treating patients with acute mania that does not respond to lithium compounds with natural isotope abundance levels.

Functionality of Li-6-Enriched Compounds

Li-6-enriched compounds offer a wide range of lithium-6 concentrations (from 10% to 95% concentrations) that may enable treatment of a broad range of psychiatric disorders, including depression, attention deficit disorder, dementia, reduced alertness, amnesia, poor memory recall, mania, bipolar disorder, and perhaps others. "Dialing" the lithium-6 concentration—for example choosing one among the eight Li-6-enriched compounds—may enable the physician to tailor the drug to fit both the psychiatric disorder and the individual patient. The freedom to finely tune not only the dose, but also the make-up of the drug itself, is a unique feature of these isotope-modified pharmaceuticals.

The four classes of compounds defined above; Li-6-purified, Li-6-enriched, Li-7-purified and Li-7-enriched, may be used to treat the following additional mental conditions, including, but not limited to: (i) seizure and epileptic disorders, (ii) obsessive compulsive disorders (OCD), attention deficit hyperactivity disorders (ADHD), border line personality disorders, impulse control disorders, phobia disorders, pain disorders, post traumatic stress disorders, seasonal effective disorders, delusional disorders, postpartum depression, dissociative disorders, stuttering disorders, acute stress disorders, eating disorders, drug withdrawal disorders, drug dependence disorders, alcohol abuse, (iii) amnesic disorders, sleep disorders, narcolepsy, catatonic disorders, (iv) autism, dyslexia, Huntington's disease, Parkinson's disease, (v) hypomanic disorders, psychotic disorders, schizophrenia, and schizoaffective disorders.

Administering Lithium isotope Modified Pharmaceuticals

Lithium carbonate (with natural isotope abundance) is prepared and administered in solid pill form that is taken orally. When multiple pills are taken daily, sometimes a morning/evening regimen is used. Isotope-modified lithium-carbonate, and other lithium compounds and salts, as described herein, can likewise be prepared in pill form, capsule, liquid, syrup form, and the like, and administered orally. Other known methods of administration can also be used, such as injections (intravenous, transdermal, intramuscular, etc.), inhalation, buccal, intranasal, and the like.

When administered for mania and bipolar disorder, lithium carbonate (with natural isotope abundance) is typically prescribed in the range from 300 mg/day up to 1500 mg/day for acute mania. Higher doses can cause kidney damage, and much higher doses can be toxic. Lower doses are ineffective. The therapeutic dosage of Li-7-enriched and Li-7-purified lithium-carbonate for treating mania and bipolar disorder may be somewhat lower, perhaps between 200 mg/day and 1200 mg/day, since the lithium-6 (that is presumed to be ineffective in tempering mania) has been switched out for a higher concentration of lithium-7. Using a lower dosage would be beneficial in reducing side effects and possible kidney damage without compromising efficacy, and even improving efficacy. With the modifications described herein, dosages lower than 300 mg/day are now possible without compromising efficacy.

The therapeutic dosage levels for Li-6-purified lithium-carbonate when treating depression or other mental conditions with reduced cognitive functioning levels is presently unknown. In the controlled experiment feeding modified lithium isotopes to female rats, the mother rats fed lithium-6 and the mother rats fed natural occurring lithium were administered the same dosage level. If this experiment on rats correctly reflects the effects of lithium isotopes on human patients, the therapeutic doses of Li-6-purified lithium carbonate in treating depression and other mental illnesses will likely fall in the same 300 mg/day to 1500 mg/day range. However, Li-6-purified compounds may be much more efficacious than compounds containing natural lithium isotope concentrations; and therefore, may still be effective at dosages below 300 mg/day, even as low as 100 mg/day.

The therapeutic dosage levels for Li-6-enriched compounds will depend on the precise lithium-6 concentration (varying throughout the range from 10% to 95% lithium-6) and the mental illness that is being treated.

The therapeutic lithium blood levels for treating mania and bipolar disorder with lithium carbonate (with natural isotope abundance) lie in the range 0.4 mM to 1.2 mM of lithium. Significantly higher blood levels can be toxic.

The therapeutic lithium blood levels for treating mania and bipolar disorder with Li-7-enriched and Li-7-purified compounds might be somewhat lower, since reduced dosages of these isotope modified compounds may be used to obtain the same efficacy as obtained using lithium with natural isotope abundances. The therapeutic lithium blood levels for treating depression and other mental disorders with reduced alertness levels with Li-6-purified compounds is not known, although the results reported in the experiment administering lithium-6 to female rats would suggest a similar blood level range (0.4 mM to 1.2 mM) as in patients with mania and bipolar disorder treated with naturally occurring lithium.

Synthesis of Isotope Modified Lithium Compounds

Both Li-6-purified (at least 95% lithium-6) and Li-7-purified (at least 99% lithium-7) lithium-carbonate can be synthesized and are now available commercially. The Li-6-enriched and Li-7-enriched class of lithium-carbonate drugs will require careful control of the lithium-6 to lithium-7 ratio in the synthesis process. This should be possible using known chemical techniques.

Lithium-Containing Compounds

The most common lithium-containing compound for treatment of mental conditions is lithium-carbonate. Naturally occurring lithium-carbonate may be modified to have the lithium-6 to lithium-7 isotope ratios discussed above to develop a therapeutically effective treatment for a range of mental conditions, including mental disorders described herein.

Lithium citrate ($Li_3C_6H_5O_7$) is also approved by the FDA for treating mania and bipolar disorder. Lithium citrate is available to be taken orally in capsules, syrup and tablets. Modifying the lithium isotope concentration, as discussed above, in lithium citrate compounds may likewise enable treatment of a broad class of mental conditions, including any of the mental disorders described above.

Lithium orotate ($LiC_5H_3N_2O_4$) and some other lithium compounds are sold across the counter as "vitamins," while lithium chloride and lithium bromide salts may be quite toxic. Modifying the lithium isotope concentrations, as discussed above, in these "vitamins" and salts might also be helpful in treating mental conditions, including any of the mental disorders described above.

The foregoing description of the preferred embodiment of the invention has been presented fir the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method for treating mental conditions, comprising administering a synthetic isotope-modified lithium-compound containing lithium-6 isotopes in an amount of at least 95% of a total number of lithium atoms in the compound, at dosages of about 100 mg/day to 1500 mg/day, whereby a symptom of the mental condition is alleviated.

2. The method of claim 1, wherein the mental condition is selected from the group consisting of depression, attention deficit disorder, dementia, reduced alertness, amnesia, and poor memory recall.

3. The method of claim 2, wherein the mental condition is depression.

4. The method of claim 3, wherein the dosages range from 100 mg/day to less than 300 mg/day.

5. The method of claim 4, wherein the compound is selected from the group consisting of lithium carbonate, lithium citrate, lithium orotate, lithium-chloride.

6. The method of claim 5, wherein the compound is lithium carbonate.

7. A method of treating mental conditions comprising administering a synthetic isotope-modified lithium-compound containing lithium-7 isotopes in an amount of at least 95% of a total number of lithium atoms in the compound, at dosages of 200 mg/day to 1200 mg/day, whereby a symptom of the mental condition is alleviated.

8. The method of claim 7, wherein the mental condition is selected from the group consisting of mania and bipolar disorder.

9. The method of claim 8, wherein the mental condition is mania.

10. The method of claim 9, wherein the lithium carbonate is administered at dosages of 200 mg/day to less than 300 mg/day.

11. The method of claim 10, wherein the compound is selected from the group consisting of lithium carbonate, lithium citrate, lithium orotate, and lithium-chloride.

12. The method of claim 11, wherein the compound is lithium carbonate.

13. A method of treating mental conditions by administering a synthetic isotope-modified lithium-compound containing lithium-6 isotopes in an amount ranging from 10% to 95% of a total number of lithium atoms in the compound, wherein the compound is administered at dosages ranging from 100 mg/day to 1500 mg/day, whereby a symptom of the mental condition is alleviated.

14. The method of claim 13, wherein the lithium-6 isotopes are present in an amount between 25% and 15% of the total number of lithium atoms in the compound.

15. The method of claim 13, wherein the lithium-6 isotopes are present in an amount between 35% and 75% of the total number of lithium atoms in the compound.

16. The method of claim 13, wherein the lithium-6 isotopes are present in an amount between 45% and 65% of the total number of lithium atoms in the compound.

17. The method of claim 13, wherein the dosages range from 100 mg/day to less than 300 mg/day.

18. The method of claim 13, wherein the mental condition is selected from the group consisting of depression, attention deficit disorder, dementia, reduced alertness, amnesia, poor memory recall, mania, and bipolar disorder.

19. The method of claim 18, wherein the mental condition is depression.

* * * * *